(12) United States Patent
Best et al.

(10) Patent No.: US 7,038,055 B2
(45) Date of Patent: May 2, 2006

(54) SULFONE DERIVATIVES AND THEIR USE IN THE TREATMENT OF AUTOIMMUNE DISEASES AND ALLERGIES

(75) Inventors: Desmond John Best, Harlow (GB); Gordon Bruton, Harlow (GB); Barry Sidney Orlek, Harlow (GB)

(73) Assignee: SmithKlineBeecham plc, Breantford (GB)

( * ) Notice: Subject to any disclaimer, the term of this patent is extended or adjusted under 35 U.S.C. 154(b) by 0 days.

(21) Appl. No.: 10/496,159

(22) PCT Filed: Nov. 25, 2002

(86) PCT No.: PCT/EP02/13263

§ 371 (c)(1),
(2), (4) Date: Nov. 24, 2004

(87) PCT Pub. No.: WO03/045922

PCT Pub. Date: Jun. 5, 2003

(65) Prior Publication Data

US 2005/0070572 A1    Mar. 31, 2005

(30) Foreign Application Priority Data

Nov. 27, 2001    (GB) ..................... 0128376

(51) Int. Cl.
C07D 215/36    (2006.01)
A61K 31/47    (2006.01)

(52) U.S. Cl. ............... 546/172; 514/311; 514/312
(58) Field of Classification Search ............... 514/312, 514/311; 546/172
See application file for complete search history.

(56) References Cited

U.S. PATENT DOCUMENTS 6,242,467 B1 * 6/2001 Faller ..................... 514/336

FOREIGN PATENT DOCUMENTS

| WO | WO 99 06361 | 2/1999 |
| WO | WO 99 38843 | 8/1999 |
| WO | WO 01/90100 | * 11/2001 |

* cited by examiner

Primary Examiner—D. Margaret Seaman
(74) Attorney, Agent, or Firm—Soma Simon; Mary McCarthy; Charles M. Kinzig

(57) ABSTRACT

A compound of formula (I) useful in the treatment and prophylaxis of conditions mediated by s-CD23

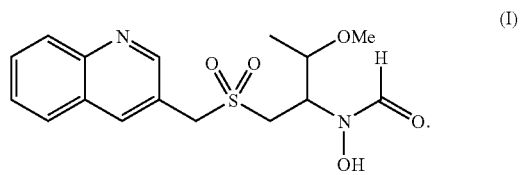

6 Claims, No Drawings

SULFONE DERIVATIVES AND THEIR USE IN THE TREATMENT OF AUTOIMMUNE DISEASES AND ALLERGIES

This invention relates to novel inhibitors of the formation of soluble human CD23 and their use in the treatment of conditions associated with excess production of soluble CD23 (s-CD23) such as autoimmune disease and allergy.

CD23 (the low affinity IgE receptor FceRII, Blast 2), is a 45 kDa type II integral protein expressed on the surface of a variety of mature cells, including B and T lymphocytes, macrophages, natural killer cells, Langerhans cells, monocytes and platelets (Delespesse et al, *Adv Immunol*, 49 [1991] 149–191). There is also a CD23-like molecule on eosinophils (Grangette et al, J Immunol, 143 [1989] 3580.3588). CD23 has been implicated in the regulation of the immune response (Delespesse et al, Immunol Rev, 125 [1992] 77–97). Human CD23 exists as two differentially regulated isoforms, a and b, which differ only in the amino acids at the intracellular N-terminus (Yokota et al, Cell, 55 [1988] 611–618). In man the constitutive a isoform is found only on B-lymphocytes, whereas type b, inducible by IL4, is found on all cells capable of expressing CD23.

Intact, cell bound CD23 (i-CD23) is known to undergo cleavage from the cell surface leading to the formation of a number of well-defined soluble fragments (s-CD23), which are produced as a result of a complex sequence of proteolytic events, the mechanism of which is still poorly understood (Bourget et al *J Biol Chem*, 269 [1994] 6927–6930). Although not yet proven, it is postulated that the major soluble fragments (Mr 37, 33, 29 and 25 kDa) of these proteolytic events, all of which retain the C-terminal lectin domain common to i-CD23, occur sequentially via initial formation of the 37 kDa fragment (Letellier et al, *J Exp Med*, 172 [1990] 693–700). An alternative intracellular cleavage pathway leads to a stable 16 kDa fragment differing in the C-terminal domain from i-CD23 (Grenier-Brosette et al, *Eur J Immunol*, 22 [1992] 1573–1577).

Several activities have been ascribed to membrane bound i-CD23 in humans, all of which have been shown to play a role in IgE regulation. Particular activities include: a) antigen presentation, b) IgE mediated eosinophil cytotoxicity, c) B cell homing to germinal centres of lymph nodes and spleen, and d) downregulation of IgE synthesis (Delespesse et al, *Adv Immunol*, 49, [1991] 149–191). The three higher molecular weight soluble CD23 fragments (Mr 37, 33 and 29 kDa) have multifunctional cytokine properties which appear to play a major role in IgE production. Thus, the excessive formation of s-CD23 has been implicated in the overproduction of IgE, the hallmark of allergic diseases such as extrinsic asthma, rhinitis, allergic conjunctivitis, eczema, atopic dermatitis and anaphylaxis (Sutton and Gould, *Nature*, 366, [1993] 421–428).

Other biological activities attributed to s-CD23 include the stimulation of B cell growth and the induction of the release of mediators from monocytes. Thus, elevated levels of s-CD23 have been observed in the serum of patients having B-chronic lymphocytic leukaemia (Sarfati et al, *Blood*, 71 [1988] 94–98) and in the synovial fluids of patients with rheumatoid arthritis (Chomarat et al, *Arthritis and Rheumatism*, 36 [1993] 234–242). That there is a role for CD23 in inflammation is suggested by a number of sources. First, sCD23 has been reported to bind to extracellular receptors which when activated are involved in cell-mediated events of inflammation. Thus, sCD23 is reported to directly activate monocyte TNF, IL-1, and IL-6 release (Armant et al, vol 180, J. Exp. Med., 1005–1011 (1994)). CD23 has been reported to interact with the B2-integrin adhesion molecules, CD11b and CD11c on monocyte/macrophage (S. Lecoanet-Henchoz et al, *Immunity*, vol 3; 119–125 (1995)) which trigger NO2$^-$, hydrogen peroxide and cytokine (IL-1, IL-6, and TNF) release. Finally, IL-4 or IFN induce the expression of CD23 and its release as sCD23 by human monocytes. Ligation of the membrane bound CD23 receptor with IgE/anti-IgE immune complexes or anti CD23 mAb activates cAMP and IL-6 production and thromboxane B2 formation, demonstrating a receptor-mediated role of CD23 in inflammation.

Because of these various properties of CD23, compounds which inhibit the formation of s-CD23 should have twofold actions of a) enhancing negative feedback inhibition of IgE synthesis by maintaining levels of i-CD23 on the surface of B cells, and b) inhibiting the immunostimulatory cytokine activities of higher molecular weight soluble fragments (Mr 37, 33 and 29 kDa) of s-CD23. In addition, inhibition of CD23 cleavage should mitigate sCD23-induced monocyte activation and mediator formation, thereby reducing the inflammatory response.

WO 99/06361 (Abbott) and WO 00/12478 (Zeneca Limited) describe a range of compounds which includes reverse hydroxamate sulfonyl and sulfonamide compounds, for use as metalloproteinase inhibitors.

WO 99/38843 (Darwin Discovery Limited) discloses a generic scope of compounds useful in the treatment of inter alia conditions mediated by enzymes involved in the shedding of CD23, which covers compounds of the formula (A):

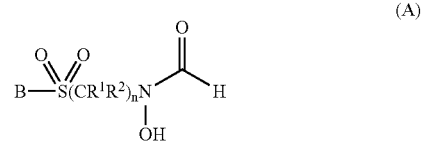

(A)

wherein B, R$^1$ and R$^2$ are selected from a range of organic groups.

PCT EPO1/05798 (SmithKline Beecham p.l.c.) discloses compounds useful in the treatment and prophylaxis of conditions mediated by enzymes involved in the shedding of CD23 which covers compounds of formula (B):

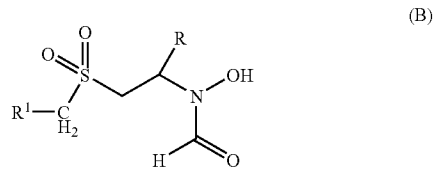

(B)

Wherein R is hydrogen, alkyl, alkenyl, alkynyl, aryl, heteroaryl or heterocyclyl; and R$^1$ is bicyclyl or heterobicyclyl.

According to the present invention, there is provided a compound of formula (I):

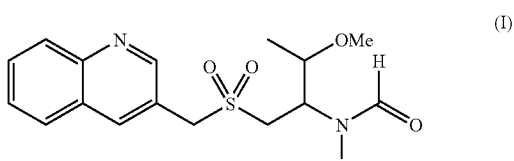

(I)

According to a further aspect, the present invention provides the use of a compound of formula (I) for the production of a medicament for the treatment or prophylaxis of disorders such allergy, allergic asthma, atopic dermatitis and other atopic diseases; inflammatory disorders; and autoimmune disease, in which the overproduction of s-CD23 is implicated.

In a further aspect the invention provides a method for the treatment or prophylaxis of disorders such as allergy, allergic asthma, atopic dermatitis and other atopic diseases; inflammatory disorders; and autoimmune disease, in which the overproduction of s-CD23 is implicated, which method comprises the administration of a compound of formula (I), to a human or non-human mammal in need thereof.

The invention also provides a pharmaceutical composition for the treatment or prophylaxis of disorders such allergy, allergic asthma, atopic dermatitis and other atopic diseases; inflammatory disorders; and autoimmune disease, in which the overproduction of s-CD23 is implicated which comprises a compound of formula (I) and optionally a pharmaceutically acceptable carrier therefor.

Particular inflammatory disorders include CNS disorders such as Alzheimer's disease, multiple sclerosis, and multi-infarct dementia, as well as the inflammation mediated sequel of stroke and head trauma.

The present inventors have surprisingly found that the compound of the invention is a highly potent and selective inhibitor of CD23 processing, having little or no activity as an inhibitor of matrix metalloproteases.

It is to be understood that the pharmaceutically acceptable salts, solvates and other pharmaceutically acceptable derivatives of the compound of formula (I) are also included in the present invention.

Salts of compounds of formula (I) include for example acid addition salts derived from inorganic or organic acids, such as hydrochlorides, hydrobromides, hydroiodides, p-toluenesulphonates, phosphates, sulphates, acetates, trifluoroacetates, propionates, citrates, maleates, fumarates, malonates, succinates, lactates, oxalates, tartrates and benzoates.

Salts may also be formed with bases. Such salts include salts derived from inorganic or organic bases, for example alkali metal salts such as sodium or potassium salts, and organic amine salts such as morpholine, piperidine, dimethylamine or diethylamine salts.

The compounds of the invention may be prepared by use of any appropriate conventional method.

In a further aspect the present invention provides a process for preparing compounds of formula (I) as defined hereinabove, which process comprises:

(a) deprotecting a compound of formula (II):

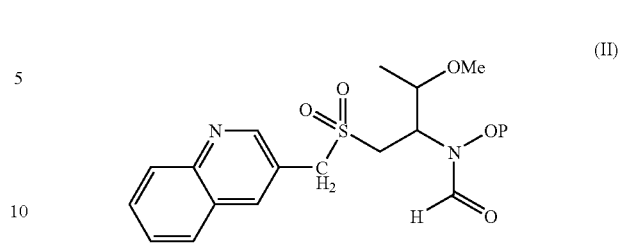

(II)

where P is a protecting group such as benzyl, tetrahydropyranyl or p-methoxybenzyl, or (b) formylating a compound of formula (III):

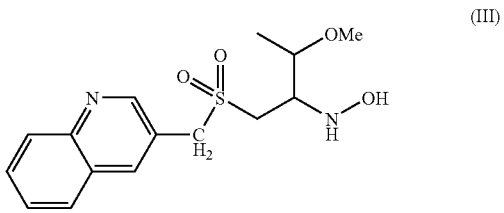

(III)

or (c) oxidising a compound of formula (X):

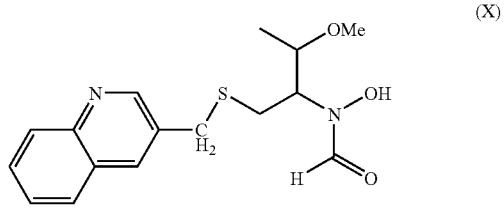

(X)

Compounds of formula (II), (III) and (X) are novel and form a further aspect of the invention.

The following reaction schemes illustrate the procedures that may be used to prepare compounds of formula (I).

Reaction Schemes

One procedure for preparing compounds of formula (I) is shown in Scheme 1. The thiol (VIII) may be prepared from the corresponding halide such as the bromide (IX) using the methods described by Choi and Yoon, Synthesis, 1995, 373, and converted into (VII) by reaction with a suitable halomethyl ketone such as the bromomethyl ketone in the presence of a base such as triethylamine. The ketone (VII) can be reacted with a suitably O-protected hydroxylamine. For example, when the protecting group (P) is benzyl, reaction with O-benzyl hydroxylamine under standard conditions can be used to prepare oxime (VI) which can be reduced to (V) with a suitable reducing agent eg sodium borohydride or sodium cyanoborohydride in acetic acid. Formylation of (V) using formic acetic anhydride followed by oxidation with meta chloroperbenzoic acid affords (II) which can be deprotected under suitable conditions.

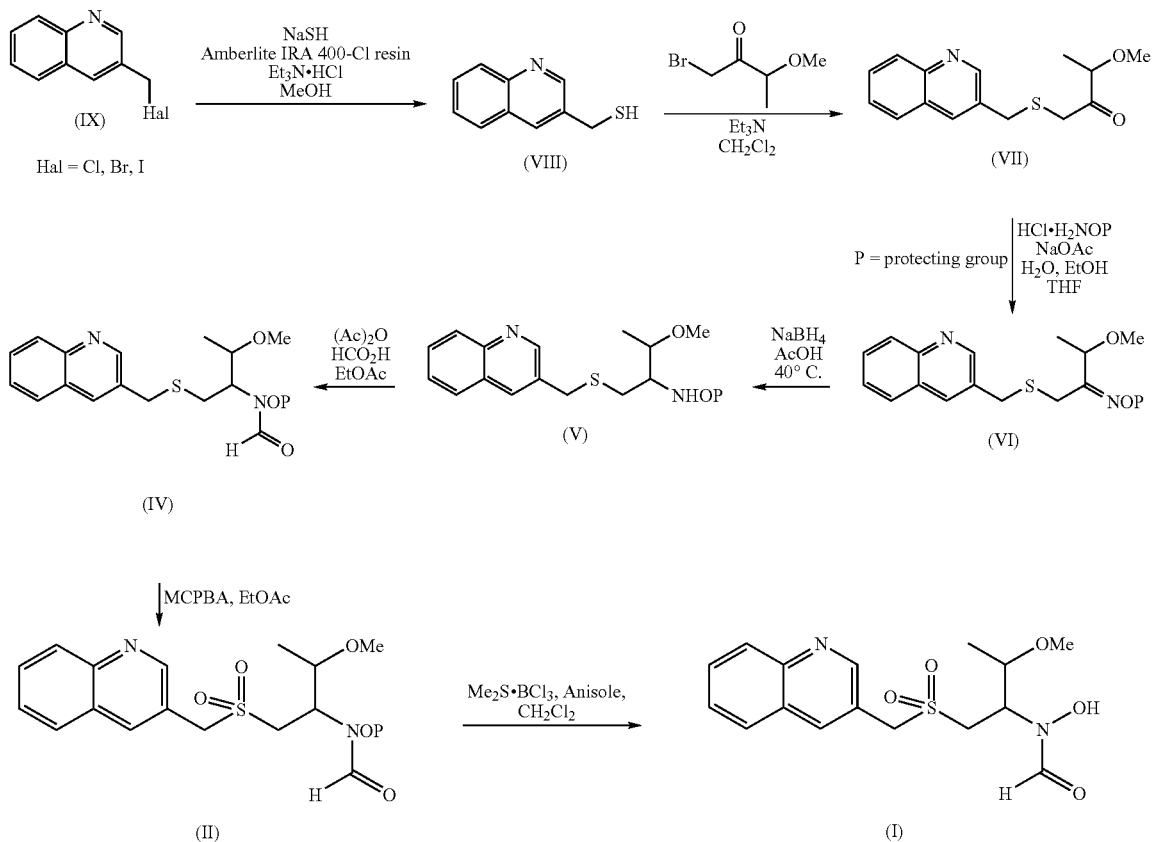

Compounds of formula (I) may also be prepared as described in Scheme 2. The ketone (VII) may be reacted with hydroxylamine under standard conditions to give an oxime (XII) which upon reduction with a suitable reducing agent such as sodium cyanoborohydride in acetic acid yields the hydroxylamine (XI) which can be formylated by treatment with formic acetic anhydride followed by potassium carbonate and methanol, and oxidised as described previously for Scheme 1.

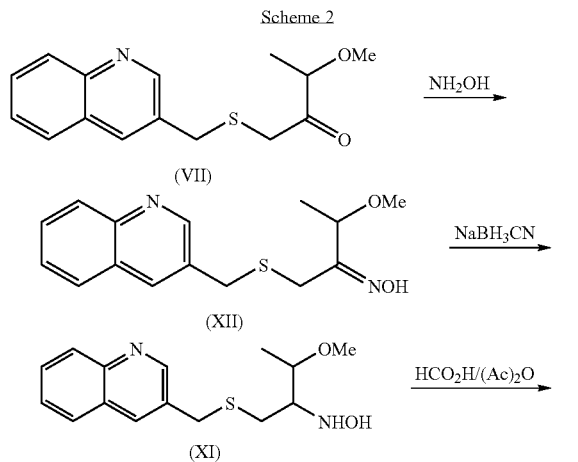

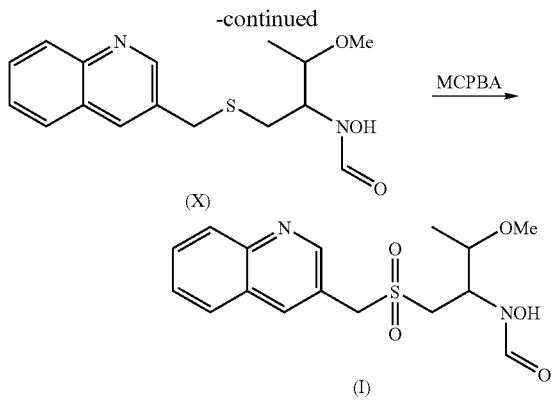

The compound of the present invention may be prepared as a mixture of isomers or as an individual isomer. The individual isomer may be prepared by any appropriate method, for example individual stereoisomers may be prepared by stereospecific chemical synthesis starting from chiral substrates or by separating mixtures of enantiomers or mixtures of diastereomers using known methods such as chiral preparative HPLC. For example, separation of compounds of formula (I) which are racemic into single enantiomers can be achieved by conversion into a suitable ester derivative such as the O-methyl mandelic acid derivative followed by separation using standard chromatographic procedures and then deprotection.

In a preferred aspect, the invention provides a compound of formula (IA):

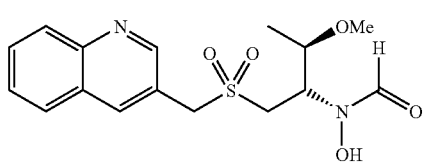

(IA)

In another preferred aspect, the invention provides a compound of formula (IB):

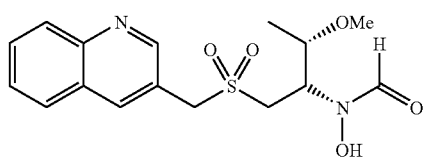

(IB)

Compounds of formula (I) can be prepared in chirally pure form using the procedures described in Scheme 3. In the preparation of compounds of formula (IA), for example, a suitably protected chiral amino alcohol (XIXA) can be converted into the corresponding thioacetate (XVIIIA) under Mitsunobu conditions eg using triphenylphosphine or tributylphosphine in combination with di-t-butylazodicarboxylate or diethylazodicarboxylate. The thioacetate (XVIIIA) can be converted in situ into a thiol and thence into the sulfide (XVIIA). Alternatively, the alcohol group in (XIXA) may be converted into a leaving group such as a tosylate or bromide and reacted with the appropriate thioacetate or thiol, such as quinolin-3-yl-methanethiol or thioacetate, in the presence of a suitable base such as sodium hydroxide to give (XVIIA). Oxidation of (XVIIA) to the sulfone (XVIA) can be carried out with a suitable oxidising agent such as MCPBA, followed by deprotection. Deprotection under standard conditions such as trifluoroacetic acid or hydrogen chloride in dioxan affords (XVA) which can be converted into (XIVA) and oxidised to the oxaziridine (XIIIA) using established procedures eg meta chloroperbenzoic acid. Conversion of the oxaziridine (XIIIA) into (IIIA) is preferably carried out using hydrochloric acid. Formylation of (IIIA) can be carried out using standard formylation methodology such as reaction with formic-acetic anhydride.

Scheme 3

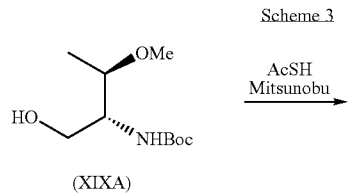

(XIXA)

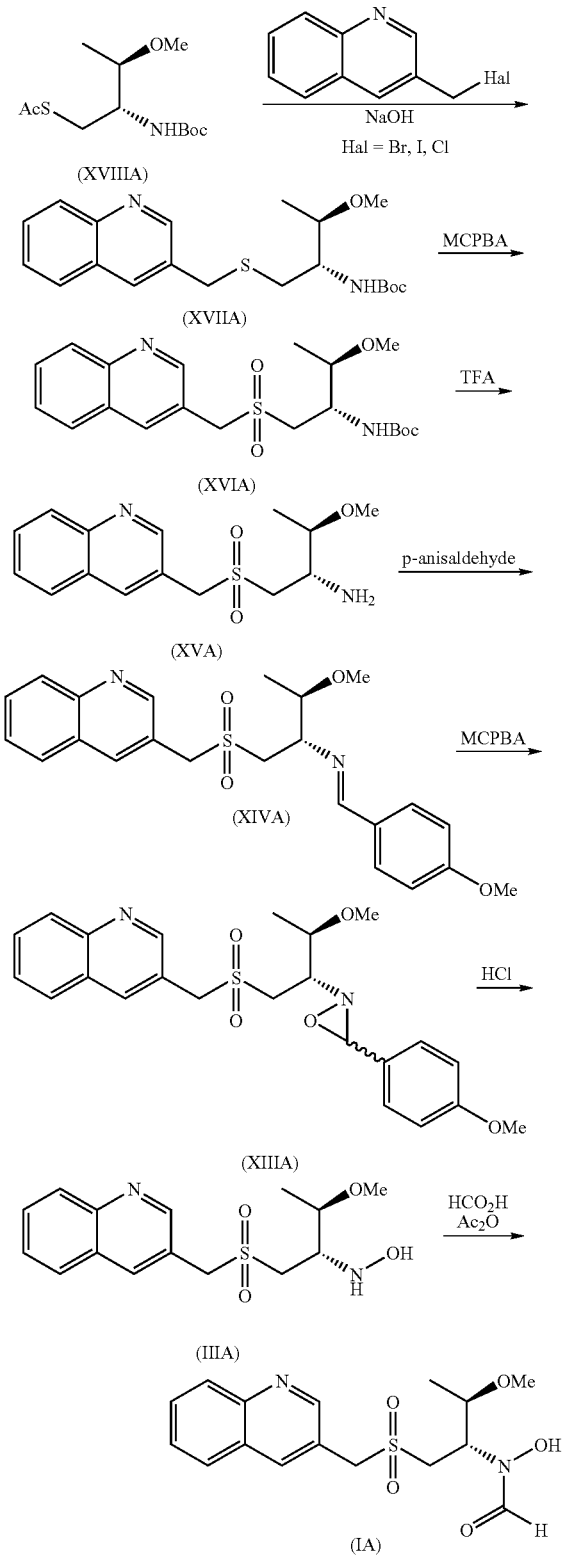

An alternative procedure for preparing compounds of formula (IIIA) in chirally pure form is shown in Scheme 4. The chiral amine (XVA) can be alkylated with cyanomethyl bromide or cyanomethyl iodide to give the cyanomethylamine (XXA) which is converted into (IIIA) using the methods described by Tokuyama et al., Synthesis, 2000, 9, 1299.

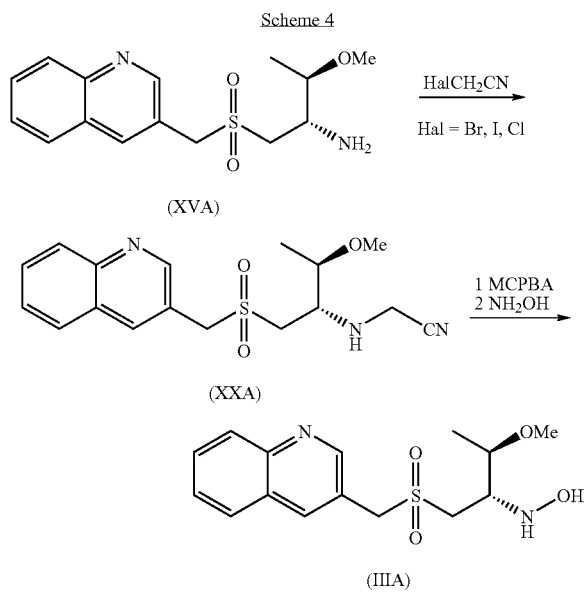

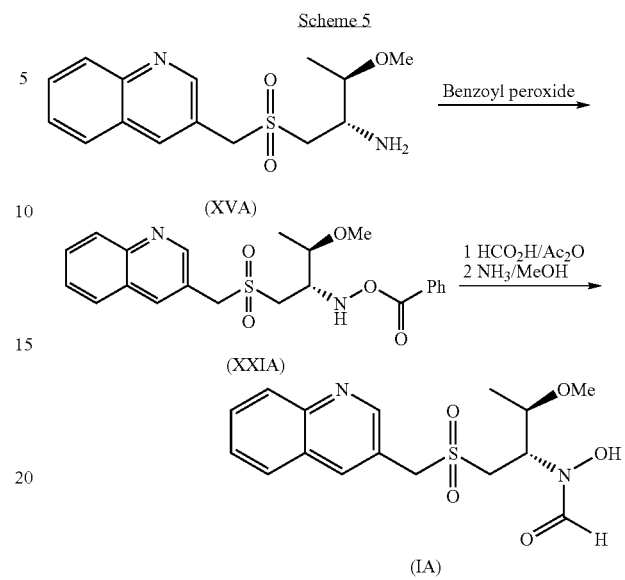

Alternatively, the amine (XVA) may be oxidised directly with benzoyl peroxide to give a benzoyl hydroxylamine (XXIA) as shown in Scheme 5, using the method described by Phanstiel, J. Org. Chem., 1997, 62,8104. The latter compound can be formylated with formic acetic anhydride and then deprotected, for example with ammonia in methanol, to give (IA).

Compounds of formula (IB) can be synthesised in an analogous manner from the appropriate chiral precursors.

Compounds of formula (III) can also be prepared using the route shown in Scheme 6. The alcohol (XXIV) can be obtained by reduction of the ketone (VII) under standard conditions, for example borane in THF. Where appropriate, the alcohol (XXIV) may be prepared by reaction of the halo alcohol (XXVI) with (XXV). Oxidation to the sulfone (XXIII) can be carried out as previously described followed by elimination using methanesulfonyl chloride and triethylamine, or Mitsunobu conditions to give (XXII). Addition of hydroxylamine to the unsaturated sulfone (XXII) affords (III).

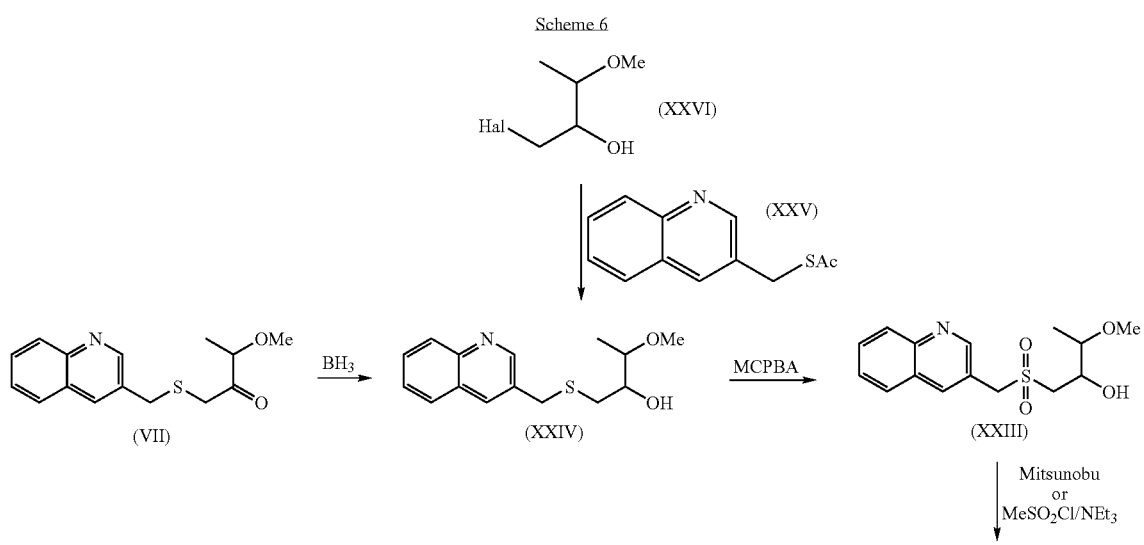

-continued

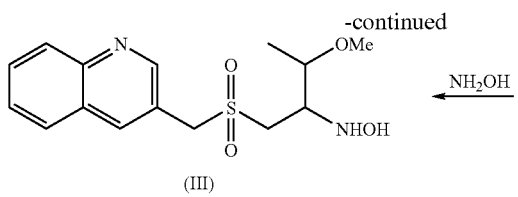

(III)

$\xleftarrow{NH_2OH}$

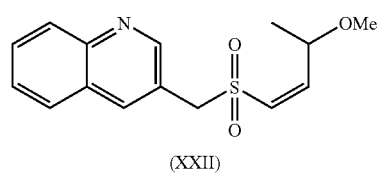

(XXII)

Halomethyl ketones can be obtained by bromination of a methyl ketone using bromine in methanol as described by Gaudry and Marquet, Org. Synth., 1976, 55, 24. Alternatively, bromomethylketones can be obtained from the corresponding diazoketones by reaction with hydrogen bromide using standard methods. Compounds of formula (IX) can be obtained by standard methods, for example by bromination of 3-methyl-quinoline with N-bromosuccinimide in carbon tetrachloride. Bromination of quinoline containing precursors with N-bromosuccinimide is preferably carried out in the presence of an acid such as acetic acid. Alternatively quinolin-3-yl-methanol may be converted into a compound of formula (IX) using standard halogenation procedures e.g. using phosphorous pentachloride or thionyl chloride, or by conversion into the mesylate followed by treatment with lithium bromide in acetone.

Protected amino alcohol precursors are either commercially available or may be prepared via standard routes e.g. from the corresponding amino acids as described by Ho et al, Tet. Lett., 1993, 34(41), 6513.

Suitable amino acid derivatives may be prepared from aziridine precursors e.g. as described by Nakajima et al., Bull. Soc. Chim. Japan, 1982, 55, 3049.

The starting materials and other reagents are available commercially or can be synthesised by well-known and conventional methods.

It is preferred that the compounds are isolated in substantially pure form.

As stated herein an inhibitor of the formation of soluble human CD23 has useful medical properties. Preferably the active compounds are administered as pharmaceutically acceptable compositions.

The compositions are preferably adapted for oral administration. However, they may be adapted for other modes of administration, for example in the form of a spray, aerosol or other conventional method for inhalation, for treating respiratory tract disorders; or parenteral administration for patients suffering from heart failure. Other alternative modes of administration include sublingual or transdermal administration.

The compositions may be in the form of tablets, capsules, powders, granules, lozenges, suppositories, reconstitutable powders, or liquid preparations, such as oral or sterile parenteral solutions or suspensions.

In order to obtain consistency of administration it is preferred that a composition of the invention is in the form of a unit dose.

Unit dose presentation forms for oral administration may be tablets and capsules and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulphate.

The solid oral compositions may be prepared by conventional methods of blending, filling or tabletting. Repeated blending operations may be used to distribute the active agent throughout those compositions employing large quantities of fillers. Such operations are of course conventional in the art. The tablets may be coated according to methods well known in normal pharmaceutical practice, in particular with an enteric coating.

Oral liquid preparations may be in the form of, for example, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia; non-aqueous vehicles (which may include edible oils), for example almond oil, fractionated coconut oil, oily esters such as esters of glycerine, propylene glycol, or ethyl alcohol; preservatives, for example methyl or propyl p-hydroxybenzoate or sorbic acid; and if desired conventional flavouring or colouring-agents.

For parenteral administration, fluid unit dosage forms are prepared utilising the compound and a sterile vehicle, and, depending on the concentration used, can be either suspended or dissolved in the vehicle. In preparing solutions the compound can be dissolved in water for injection and filter sterilised before filling into a suitable vial or ampoule and sealing. Advantageously, adjuvants such as a local anaesthetic, a preservative and buffering agents can be dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration. The compound can be sterilised by exposure to ethylene oxide before suspending in the sterile vehicle. Advantageously, a surfactant or wetting agent is included in the composition to facilitate uniform distribution of the compound.

Compositions of this invention may also suitably be presented for administration to the respiratory tract as a snuff or an aerosol or solution for a nebulizer, or as a microfine powder for insufflation, alone or in combination with an inert carrier such as lactose. In such a case the particles of active compound suitably have diameters of less than 50 microns, preferably less than 10 microns for example diameters in the range of 1–50 microns, 1–10 microns or 1–5 microns. Where appropriate, small amounts of other anti-asthmatics and bronchodilators, for example sympathomimetic amines such as isoprenaline, isoetharine, salbutamol, phenylephrine and ephedrine; xanthine derivatives such as theophylline and aminophylline and corticosteroids such as prednisolone and adrenal stimulants such as ACTH may be included.

The compositions may contain from 0.1% to 99% by weight, preferably from 10–60% by weight, of the active material, depending upon the method of administration. A preferred range for inhaled administration is 10–99%, especially 60–99%, for example 90, 95 or 99%.

Microfine powder formulations may suitably be administered in an aerosol as a metered dose or by means of a suitable breath-activated device.

Suitable metered dose aerosol formulations comprise conventional propellants, cosolvents, such as ethanol, surfactants such as oleyl alcohol, lubricants such as oleyl alcohol, desiccants such as calcium sulphate and density modifiers such as sodium chloride.

Suitable solutions for a nebulizer are isotonic sterilised solutions, optionally buffered, at for example between pH 4–7, containing up to 20 mg/ml of compound but more generally 0.1 to 10 mg/ml, for use with standard nebulisation equipment.

An effective amount will depend on the relative efficacy of the compounds of the present invention, the severity of the disorder being treated and the weight of the sufferer. Suitably, a unit dose form of a composition of the invention may contain from 0.1 to 1000 mg of a compound of the invention (0.001 to 10 mg via inhalation) and more usually from 1 to 500 mg, for example 1 to 25 or 5 to 500 mg. Such compositions may be administered from 1 to 6 times a day, more usually from 2 to 4 times a day, in a manner such that the daily dose is from 1 mg to 1 g for a 70 kg human adult and more particularly from 5 to 500 mg. That is in the range of about 1.4×10 m 2 mg/kg/day to 14 mg/kg/day and more particularly in the range of about 7×10-2 mg/kg/day to 7 mg/kg/day.

The Following Examples Illustrate the Invention but do not Limit it in Any Way

Preparation 1: 3-chloromethylquinoline hydrochloride

Step 1: 3-Quinolylmethanol—Quinoline-3-carboxaldehyde (13.18 g) in ethanol (260 ml) was cooled to 0° C. followed by the addition of sodium borohydride (1.62 g) portionwise. The temperature was maintained at 0° C. for 15 min followed by the addition of 6N HCl (28 ml) during which time the temperature of the reaction was maintained between 0–5° C. The solution was then neutralised with 1M NaOH. The crude reaction mixture was stripped to dryness to remove ethanol and the residue was partitioned between water and EtOAc. The EtOAc layer was then dried (MgSO₄) and absorbed onto silica gel and chromatographed (flash silica gel, step gradient: 0–100% EtOAc/hexane) to give the subtitle compound as a white solid (9.85 g).

Step 2: 3-Chloromethylquinoline hydrochloride—3-Quinolylmethanol (9.85 g) was taken up in dry benzene (200 ml) and stirred followed by the addition of thionyl chloride (14.69 ml). An immediate yellow precipitate was obtained. Stirring was maintained at rt for 2 h. A light yellow solid was filtered off and dried to give the subtitle compound (13 g).

EXAMPLE 1

N-[(2S,3R)-3-methoxy-1-(quinolin-3-yl-methanesulfonyl)butan-2-yl]-hydroxyformamide

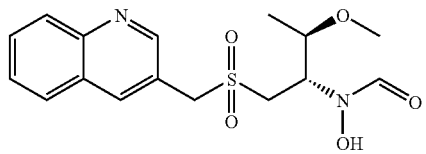

Step 1: (2S,3R)-2-N-t-Butoxycarbonylamino-3-methoxybutanoic acid

An ice-cold solution of (2S,3R)-2-amino-3 methoxybutanoic acid (1.04 g) in 1,4-dioxan (10 ml) and 1M sodium hydroxide (7.82 ml) solution was treated with di-t-butyl-dicarbonate (1.88 g). The mixture was allowed to gain room temperature and stirred overnight. The solution was washed with hexane (3×5 ml), acidified with 5% citric acid solution and extracted with ethyl acetate (25 ml). The organic phase was dried (MgSO₄) and evaporated to give the subtitle compound (1.81 g) $^1$H δ(CDCl₃) 5.3 (1H,m), 4.35 (1H,m), 3.98 (1H,d,J=6.5 Hz), 3.39 (3H,s), 1.46 (9H,s), 1.21 (3H,d,J=6.5 Hz).

Step 2: (2R,3R)-2-N-t-Butoxycarbonylamino-3-methoxybutanol

A stirred solution of (2S,3R)-2-N-t-butoxycarbonylamino-3-methoxybutanoic acid (1.75 g) in dry THF (20 ml) at −10° C. was treated with N-methylmorpholine (0.83 ml) and isobutyl chloroformate (0.98 ml). After 30 min the mixture was filtered and recooled in ice. A solution of sodium borohydride (0.285 g) in water (5 ml) was added and the mixture stirred for 1 h. After acidification to pH3 with 1M hydrochloric acid the mixture was extracted with ethyl acetate (20 ml). The extract was washed with water (2×10 ml), saturated brine (10 ml), dried (MgSO₄) and evaporated to yield the subtitle compound (1.2 g) $^1$H NMR δ(CDCl₃): 5.1(1H,m), 3.59–3.75 (4H,m), 3.33 (3H,s), 1.45(9H,t), 1.18 (3H,d,J=6.8 Hz), Step 3: (2S,3R)-2-N-t-Butoxycarbonylamino-3-methoxybutyl thioacetate An ice-cold solution of triphenylphosphine (2.75 g) in THF (40 ml) was treated dropwise with diisopropyl azodicarboxylate (2.07 ml) and stirred for 30 min. A solution of (2R,3R)-2-N-t-butoxycarbonylamino-3-methoxybutanol (1.15 g) and thioacetic acid (0.75 ml) in THF (10 ml) was added dropwise. The reaction was allowed to gain rt overnight and evaporated. The residue was extracted with hexane (150 ml), evaporated and flash chromatographed (silica gel, step gradient: 0–5% EtOAc/MDC) to give the subtitile compound (1.24 g). $^1$H NMR δ(CDCl₃): 4.82 (1H, broad d), 3.66 (1H, m), 3.42 (1H,m), 3.31 (3H,s), 2.96–3.18 (2H, m), 2.32 (3H, s), 1.42 (9H, s), 1.13 (3H, d, J=6.3 Hz), Step 4: (2S,3R)-2-(N-t-Butoxycarbonylamino)-3-methoxy-1-(3-quinolylmethanesulfanyl)-butane A stirred mixture of (2S,3R)-2-N-t-butoxycarbonylamino-3-methoxybutyl thioacetate (1.05 g) and 3-chloromethylquinoline hydrochloride (0.61 g) in methanol (50 ml) at rt was treated dropwise with 1M sodium hydroxide (5.7 ml) and stirred overnight. The mixture was evaporated to low volume and diluted with saturated sodium hydrogen carbonate solution (10 ml). After extraction with MDC (2×10 ml), the combined extracts were dried (MgSO₄) and evaporated. The residue was flash chromatographed (silica gel, step gradient: 15–30% EtOAc/MDC) to give the subtitle compound (1.31 g). MS (APCI+ve ion) 377(MH⁺); ¹H NMR δ(CDCl₃): 8.9 (1H, m), 8.1 (2H, m), 7.79 (1H, d, J=8 Hz), 7.69 (1H, t, J=8 Hz), 7.56(1H, t, J=8 Hz), 4.87 (1H, broad d), 3.91 (2H, s), 3.68 (2H, m), 3.27 (3H,s), 2.55 (2H, m), 1.46 (9H, s), 1.15 (3H, d,J=6.3 Hz).

Step 5: (2S,3R)-2-(N-t-Butoxycarbonylamino)-3-methoxy-1-(3-quinolylmethanesulfonyl)-butane An ice-cold solution of (2S,3R)-2-(N-t-butoxycarbonylamino)-3-methoxy-1-(3-quinolylmethanesulfanyl)buta (1.3 g) in MDC (20 ml) was treated with 50% 3-chloroperoxybenzoic acid (2.1 g) and the mixture stirred for 1 h. The reaction mixture was quenched with 10% sodium thiosulfate (10 ml) followed by saturated sodium bicarbonate (10 ml) solution. After 5 min the organic phase was collected, dried (MgSO₄) and evaporated. The residue was crystallised from ethyl acetate-hexane mixtures to give the subtitle compound (1 g). MS (APCI+ve ion) 397(MNa⁺); ¹H NMR δ(CDCl₃): 8.9 (1H, m), 8.3 (1H, d, J=2 Hz), 8.1 (1H d, J=8 Hz), 7.83 (1H, d, J=8 Hz), 7.75 (1H, t, J=8 Hz), 7.53 (1H,d,J=8 Hz), 5.04 (1H, broad), 4.6 (2H, m), 4.2 (1H, m), 3.71 (1H,m), 3.31 (3H,s), 3.17 (2H,m), 1.55(9H,m), 1.19 (3H, d, J=6.3 Hz).

Step 6: (2S,3R)-2-Amino-3-methoxy-1-(3-quinolylmethanesulfonyl)butane dihydrochloride A stirred solution of (2S,3R)-2-(N-t-butoxycarbonylamino)-3-methoxy-1-(3-quinolylmethanesulfonyl)butane (1 g) in MDC (10 ml) at rt was treated with 4M hydrogen chloride in dioxan (10 ml). After 1 h the mixture was evaporated to give the subtitle compound (0.93 g). MS (APCI+ve ion) 309 (MH⁺), ¹H NMR δ(DMSO-d6) 9.04 (1H, m), 8.71 (1H, s), 8.3 (3H, broad s), 8.2 (2H, m), 7.91 (1H, t, J=8 Hz), 7.78 (1H, t, J=8 Hz), 5.08 (2H, m), 3.3–3.88 (4H, m), 3.31 (3H,s), 1.7 (2H, m), 1.19 (3H, d,J=6.3 Hz), Step 7: (2S,3R)-2-(N-Cyanomethylamino)-3-methoxy-1-(3-quinolylmethanesulfonyl)butane A mixture of (2S,3R)-2-amino-3-methoxy-1-(3-quinolylmethanesulfonyl)butane dihydrochloride (0.93 g), bromoacetonitrile (0.41 ml) and N-ethyldiisopropylamine (1.7 ml) in acetonitrile (15 ml) was refluxed for 16 h, cooled and evaporated. The residue was partitioned between MDC (15 ml) and saturated sodium hydrogen carbonate solution (15 ml). The organic phase was collected and the aqueous re-extracted with MDC (15 ml). The combined MDC phases were dried (MgSO₄) and evaporated. The residue was flash chromatographed (silica gel, step gradient: 70–100% EtOAc/hexane) to give the subtitle compound (0.59 g). MS (APCI+ve ion) 348(MH⁺); ¹H NMR δ(CDCl₃): 8.91 (1H, m), 8.3 (1H, d, J=2 Hz), 8.14 (1H, d, J=8 Hz), 7.78 (1H, d, J=8 Hz), 7.78 (1H, t, J=8 Hz), 7.60 (1H, t, J=8 Hz), 4.55 (2H, s), 3.4–3.88 (4H, m), 3.33 (3H, s), 2.93–3.28 (2H, m), 2.18 (1H, m), 0.93 (3H, d, J=6.3 Hz).

Step 8: (2S,3R)-N-[3-methoxy-1-(3-quinolylmethanesulfonyl)-butan-2-yl]hydroxylamine An ice-cold stirred solution of (2S,3R)-3-methoxy-2-(N-cyanomethylamino)-1-(3-quinolylmethanesulfonyl)butane (590 mg) in MDC (20 ml) was treated with 4-toluenesulphonic acid monohydrate (50 mg) and 70% 3-chloroperoxybenzoic acid (281 mg). After 45 min the reaction was quenched with 10% sodium thiosulphate (5 ml) followed by saturated sodium hydrogen carbonate (5 ml) solution. After 5 min the organic layer was collected and the aqueous re-extracted with MDC (10 ml). The combined MDC phases were dried (MgSO₄) and evaporated. The residue was redissolved in methanol (10 ml) treated with 4-toluenesulphonic acid monohydrate and hydroxylamine hydrochloride (2.36 g) and heated at 60° C. for 1.5 h. The cooled solution was evaporated, then dissolved in water (5 ml) and saturated sodium hydrogen carbonate solution (5 ml). After extraction with MDC (2×5 ml), the combined extracts were dried (MgSO₄) and evaporated. The residue was flash chromatographed (silica gel, step gradient: 80–100% ethyl acetate in hexane) to give the subtitle compound (305 mg). MS (APCI+ve ion) 325(MH⁺); ¹H NMR δ(CDCl₃): 8.91 (1H, m), 8.32 (1H, d, J=2 Hz), 8.14 (1H, d, J=8 Hz), 7.85 (1H, d, J=8 Hz), 7.76 (1H, t, J=8 Hz), 7.6 (1H, t, J=8 Hz), 4.83 (1H, broad), 4.58 (2H, m), 3.0–3.7 (4H, m), 3.38 (3H, s), 0.92 (3H, d, J=6.3 Hz).

Step 9: N-[(2S,3R)-3-methoxy-1-(quinolin-3-yl-methanesulfonyl)butan-2-yl]-N-hydroxyformamide (2S,3R)-N-[3-Methoxy-1-(3-quinolylmethanesulfonyl)-2-butyl]hydroxylamine (300 mg) was dissolved in a pre-mixed solution of acetic anhydride (2 ml) and formic acid (6 ml) and stood overnight. The reaction was evaporated and then re-evaporated from chloroform (2×5 ml). The residue was redissolved in methanol (5 ml), treated with potassium carbonate (639 mg) and stirred for 45 min and then evaporated. The residue was redissolved in water (5 ml) and the pH adjusted to 7 with 1M hydrochloric acid. After extraction with MDC (2×5 ml), the combined extracts were dried (MgSO₄) and evaporated. The residue was chromatographed (acid washed silica gel, 3% MeOH/MDC) to give the title compound (232 mg). MS (APCI+ve ion) 353 (MH⁺); ¹H NMR δ[(CD₃)₂SO] 9.9 and 9.7 (1H, 2xs rotamers), 8.83 (1H, m), 8.38 (1H,d,J=2 Hz), 8.32 and 8.0 (1H,2xs rotamers), 8.03 (2H, m), 7.81 (1H, t, J=8 Hz), 7.66 (1H, t, J=8 Hz), 4.85 and 4.22(1H, 2xs rotamers), 4.76 (2H, m), 3.7–3.3 (3H, m), 3.25 (3H, s), 1.15 (3H, m rotamers).

EXAMPLE 2

N-[(2R,3S)-3-methoxy-1-(quinolin-3-yl-methanesulfonyl)butan-2-yl]-hydroxyformamide

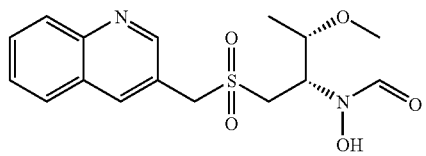

The compound of Example 2 was prepared from 2R,3S)-2-amino-3 methoxybutanoic acid using a similar process to that described in Example 1.

BIOLOGICAL TEST METHODS

Procedure 1: The ability of test compounds to inhibit the release of soluble CD23 was investigated by use of the following procedure.

RPMI 8866 Cell Membrane CD23 Cleavage Activity Assay:

Plasma membranes from RPMI 8866 cells, a human Epstein-Barr virus transformed B-cell line (Sarfati et al., Immunology 60 [1987] 539–547) expressing high levels of CD23 are purified using an aqueous extraction method. Cells resuspended in homogenization buffer (20 mM HEPES pH 7.4, 150 mM NaCl, 1.5 mM MgCl2, 1 mM DTT)

are broken by N$_2$ cavitation in a Parr bomb and the plasma membrane fraction mixed with other membranes is recovered by centrifugation at 10,000×g. The light pellet is resuspended in 0.2 M potassium phosphate, pH 7.2 using 2 ml per 1–3 g wet cells and the nuclear pellet is discarded. The membranes are further fractionated by partitioning between Dextran 500 (6.4% w/w) and polyethylene glycol (PEG) 5000 (6.4% w/w) (ref), at 0.25 M sucrose in a total of 16 g per 10–15 mg membrane proteins [Morre and Morre, BioTechniques 7, 946–957 (1989)]. The phases are separated by brief centrifugation at 1000×g and the PEG (upper) phase is collected, diluted 3–5 fold with 20 mM potassium phosphate buffer pH 7.4, and centrifuged at 100,000×g to recover membranes in that phase. The pellet is resuspended in phosphate-buffered saline and consists of 3–4 fold enriched plasma membranes as well as some other cell membranes (e.g. lysosomes, Golgi). The membranes are aliquoted and stored at −80° C. Fractionation at 6.6% Dextran/PEG yields plasma membranes enriched 10-fold.

The fractionated membranes are incubated at 37° C. for times up to 4 hrs to produce fragments of CD23 which are separated from the membrane by filtration in 0.2 micron Durapore filter plates (Millipore) after quenching the assay with a non-selecitve MMP inhibitor, e.g. 5 uM Preparation 1 from WO 95/31457 ([4-(N-Hydroxyamino)-2-(R)-isobutyl-3-(S)-(2-thiophenethiomethyl)succinyl]-(S)-phenylalanine-N-methylamide sodium salt, prepared according to the procedure described in Example 11 of WO 90/05719). sCD23 released from the membrane is determined using the EIA kit from The Binding Site (Birmingham, UK) or a similar one utilising MHM6 anti-CD23 mAb [Rowe et al., Int. J. Cancer, 29, 373–382 (1982)] or another anti-CD23 mAb as the capture antibody in a sandwich EIA. The amount of soluble CD23 made by 0.5 ug membrane protein in a total volume of 50 ul phosphate-buffered saline is measured by EIA and compared to the amount made in the presence of various concentrations of inhibitors. Inhibitors are prepared in solutions of water or dimethylsulfoxide (DMSO) and the final DMSO concentration is not more than 2%. IC50's are determined by curve fitting as the concentration where 50% inhibition of production of sCD23 is observed relative to the difference in sCD23 between controls incubated without inhibitor.

Results

The compound of Example 1 showed an IC$_{50}$ value of 0.02 uM

The compound of Example 2 showed an IC$_{50}$ value of 0.04 uM

Procedure 2: The ability of test compounds to inhibit matrix metalloproteases was investigated using the following procedures.

Collagenase Inhibition Assay:

The potency of compounds to act as inhibitors of collagenase was determined by the method of Cawston and Barrett (Anal. Biochem. 99, 340–345, 1979), hereby incorporated by reference, whereby a 1 mM solution of the inhibitor being tested or dilutions thereof, was incubated at 37° C. for 18 h with collagen and human recombinant collagenase, from synovial fibroblasts cloned, expressed and purified from *E. Coli*, (buffered with 150 mM Tris, pH 7.6, containing 15 mM calcium chloride, 0.05% Brij 35, 200 mM sodium chloride and 0.02% sodium azide). The collagen was acetylated $^3$H type 1 bovine collagen prepared by the method of Cawston and Murphy (methods in Enzymology 80, 711, 1981) The samples were centrifuged to sediment undigested collagen and an aliquot of the radioactive supernatant removed for assay on a scintillation counter as a measure of hydrolysis. The collagenase activity in the presence of 1 mM inhibitor, or dilution thereof, was compared to activity in a control devoid of inhibitor and the results reported as that concentration effecting 50% of the collagenase (IC$_{50}$).

Results

The compound of Example 1 showed an IC$_{50}$ value of >10 uM in procedure 2.

General MMP Inhibition Assays:

Inhibition of matrix metalloprotease activity was determined using a fluorescence quench assay with appropriate substrate. For example, MMP activity was determined using MMP activated using trypsin, according to Lark et al, Connective Tissue Res. 25, 52 (1990). The MMP is incubated at room temperature in a microtitre plate in a total volume of 100 ul, containing 0.15 M Tris Cl, 15 mM CaCl2, 0.2 M NaCl, pH 7.6 (assay buffer); inhibitor at concentrations up to 100 uM, with no more than 2% DMSO final concentration, 10 uM substrate (such as SDP-3815-PI for MMP-1, Peptides International). The MMP concentration is <10 nM, and determined empirically with the appropriate substrate to give at least a 20-fold increase in fluorescence emission in 30 min. Fluorescent excitation wavelength was 355 nm, emission wavelength 400–460 nm, and data points are collected to generate slope (change in fluorescence with time). Percent inhibition for each concentration is calculated from the slope at time zero, and IC50 values from the concentration dependence. MMP-1, 2, 3, 7, 9, 13, 14 may all be assayed in the same manner, using commercially available substrates reported to be effective for each enzyme. Enzymes were obtained from Calbiochem and activated using the same trypsin method.

Results

The compound of Example 1 showed an IC$_{50}$ value of >10 uM vs MMP-3 and an IC$_{50}$ value of =2.6 uM vs MMP-13.

The compound of Example 2 showed an IC$_{50}$ value of 3 uM vs MMP-13.

Abbreviations

Bn—benzyl

EtOAc—ethyl acetate h—hour min—minutes

MCPBA—meta chloroperoxybenzoic acid

MDC—dichloromethane rt—room temperature

THR—tetrahydrofuran

The invention claimed is:

1. A compound of formula (I):

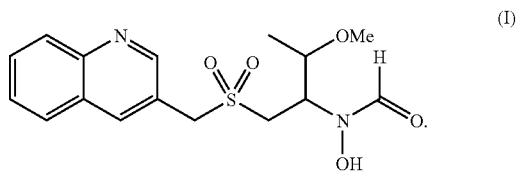

2. A compound of formula (IA):
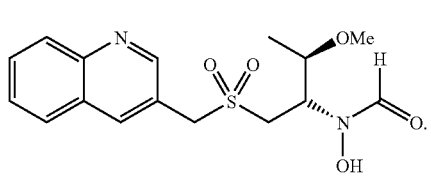
3. A compound of formula (IB):
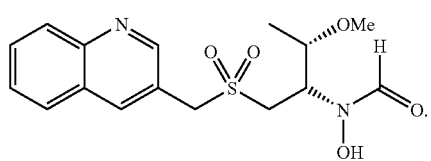
4. A pharmaceutical composition for the treatment or prophylaxis of disorders in which the overproduction of s-CD23 is implicated which comprises a compound according to claim 1 and optionally a pharmaceutically acceptable carrier therefor.
5. A compound of formula (III):
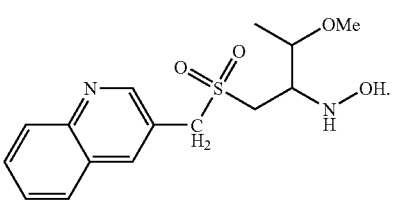
6. A compound of formula (X):
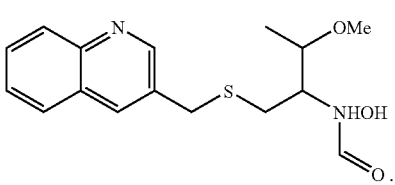
* * * * *